(12) United States Patent
Michihata et al.

(10) Patent No.: US 11,445,888 B2
(45) Date of Patent: Sep. 20, 2022

(54) IMAGE PROCESSING APPARATUS AND IMAGE PROCESSING METHOD

(71) Applicant: Sony Olympus Medical Solutions Inc., Tokyo (JP)

(72) Inventors: Taihei Michihata, Tokyo (JP); Hiroshi Myoken, Tokyo (JP); Satoshi Mitsui, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 2 days.

(21) Appl. No.: 17/149,759

(22) Filed: Jan. 15, 2021

(65) Prior Publication Data

US 2021/0282623 A1 Sep. 16, 2021

(30) Foreign Application Priority Data

Mar. 13, 2020 (JP) ................................ JP2020-044677

(51) Int. Cl.
| | |
|---|---|
| *A61B 1/00* | (2006.01) |
| *H04N 5/225* | (2006.01) |
| *A61B 1/05* | (2006.01) |
| *G06K 15/02* | (2006.01) |
| *H04N 1/60* | (2006.01) |

(52) U.S. Cl.
CPC ............ *A61B 1/00009* (2013.01); *A61B 1/05* (2013.01); *G06K 15/1878* (2013.01); *H04N 1/6016* (2013.01); *H04N 5/22541* (2018.08); *H04N 2005/2255* (2013.01)

(58) Field of Classification Search
CPC .................. A61B 1/00009; A61B 1/05; A61B 1/000095; A61B 1/045; G06K 15/1878; H04N 1/6016; H04N 5/22541; H04N 2005/2255; H04N 9/67
See application file for complete search history.

(56) References Cited

U.S. PATENT DOCUMENTS

| | | | | |
|---|---|---|---|---|
| 6,701,024 B1* | 3/2004 | Sasai | ...................... | H04N 1/409 382/274 |
| 6,788,339 B1* | 9/2004 | Ikeda | ...................... | H04N 9/735 348/223.1 |
| 2015/0296193 A1* | 10/2015 | Cote | .................. | H04N 9/04557 382/167 |
| 2019/0238866 A1* | 8/2019 | Ström | .................... | H04N 19/86 |

\* cited by examiner

*Primary Examiner* — Richard T Torrente
(74) *Attorney, Agent, or Firm* — Xsensus LLP

(57) ABSTRACT

An image processing apparatus includes a linear matrix operation unit configured to set a matrix coefficient in accordance with an input image signal, and perform a linear matrix operation on the image signal using the set matrix coefficient.

7 Claims, 12 Drawing Sheets

IMAGE PROCESSING APPARATUS AND IMAGE PROCESSING METHOD

CROSS-REFERENCE TO RELATED APPLICATION

This application claims priority from Japanese Application No. 2020-044677, filed on Mar. 13, 2020, the contents of which are incorporated by reference herein in its entirety.

BACKGROUND

The present disclosure relates to an image processing apparatus and an image processing method.

There is a known image processing apparatus that performs image processing on an image signal generated by imaging an observation target using an imaging device. Spectral characteristics of an imaging device deviate from ideal RGB characteristics, and thus, using RGB signals as they are without any correction would lead to low color reproducibility. To cope with this, the image processing apparatus performs a linear matrix operation of converting the RGB signals by a 3×3 matrix to bring the RGB signals closer to the ideal RGB characteristics (refer to JP 2013-26987 A, for example).

SUMMARY

The linear matrix operation has no optimal solution that brings all colors closer to ideal RGB. In addition, there is a case where an attempt to bring a certain color closer to the ideal RGB would bring the other colors to non-existent colors (for example, the luminance Y in negative values). When such an error occurs, the known image processing apparatus controls to reduce the correction coefficient in the linear matrix operation to prevent malfunction, making it difficult to ensure sufficient color reproducibility in some cases.

There is a need for an image processing apparatus and an image processing method capable of preventing malfunction while ensuring color reproducibility in the linear matrix operation.

According to one aspect of the present disclosure, there is provided an image processing apparatus including a linear matrix operation unit configured to set a matrix coefficient in accordance with an input image signal, and perform a linear matrix operation on the image signal using the set matrix coefficient.

DETAILED DESCRIPTION

Figure 1:
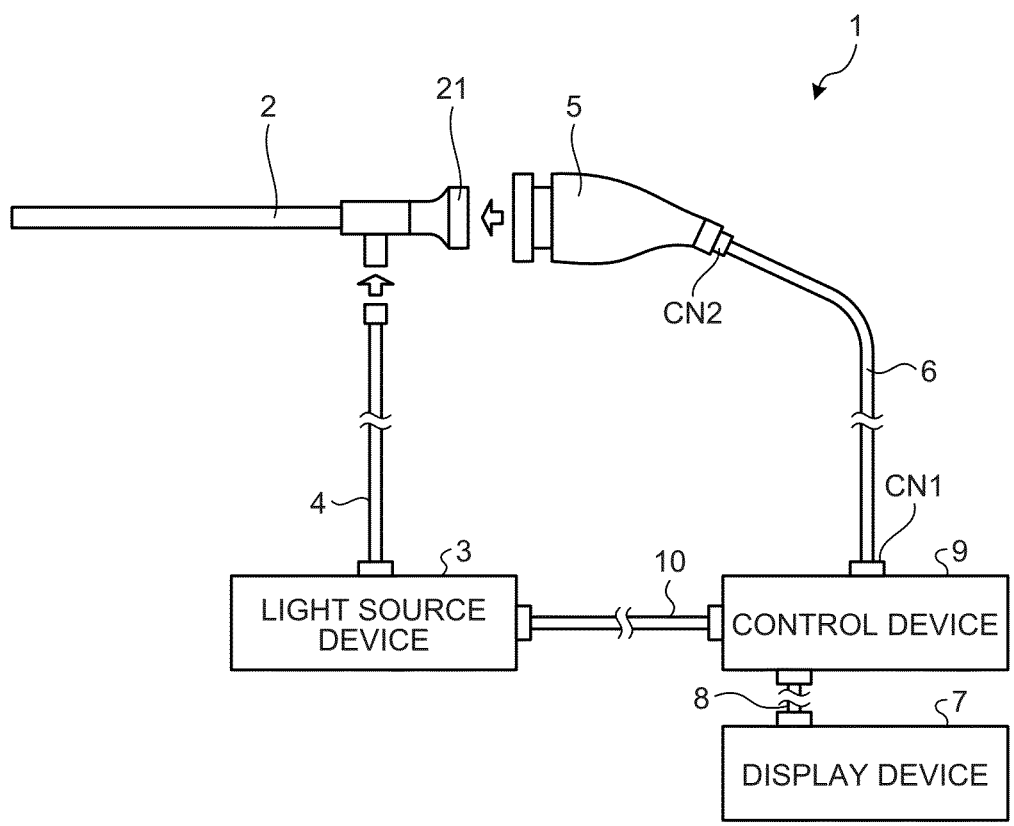
FIG. 1 is a schematic diagram illustrating a configuration of an observation apparatus including an image processing apparatus according to a first embodiment.

Hereinafter, modes for carrying out the present disclosure (hereinafter referred to as embodiments) will be described with reference to the drawings. Note that the present disclosure is not limited to the embodiments described below. In the drawings, same reference signs are attached to the same components.

First Embodiment

Configuration of Observation System

FIG. 1 is a schematic diagram illustrating a configuration of an observation apparatus including an image processing apparatus according to a first embodiment. An observation apparatus 1 is an apparatus used in the medical field to observe internal portions of a living organism. As illustrated in FIG. 1, the observation apparatus 1 includes an insertion portion 2, a light source device 3, a light guide 4, a camera head 5, a first transmission cable 6, a display device 7, a second transmission cable 8, a control device 9, and a third transmission cable 10.

In the present embodiment, the insertion portion 2 is constituted with a rigid endoscope. That is, the insertion portion 2 has an elongated shape that is entirely rigid, or partially rigid with a partially flexible portion, so as to be inserted into a living organism. The insertion portion 2 includes an optical system having one or more lenses and configured to collect light (subject image) from the living organism. However, the insertion portion 2 may be a flexible endoscope.

The light source device 3 is connected to one end of the light guide 4, and supplies light for illuminating the inside of the living organism to the one end of the light guide 4 under the control of the control device 9. In the present embodiment, the light source device 3 is separated from the control device 9. However, the configuration is not limited to this, and it is allowable to employ a configuration in which the light source device 3 is provided inside the control device 9.

The light guide 4 has one end detachably connected to the light source device 3 and the other end detachably connected to the insertion portion 2. The light guide 4 transmits the light supplied from the light source device 3 from one end to the other end and supplies the light to the insertion portion 2. The light supplied to the insertion portion 2 is emitted from a distal end of the insertion portion 2 and directed into the living organism. The light (subject image) applied to internal portions of the living organism is collected by the optical system in the insertion portion 2.

The camera head 5 is detachably connected to a proximal end (an eyepiece 21 (FIG. 1)) of the insertion portion 2. The camera head 5 captures the subject image collected by the insertion portion 2 under the control of the control device 9, and outputs an image signal (RAW signal) obtained by the imaging. The image signal is an image signal of 4K resolution or more.

The first transmission cable 6 has one end detachably connected to the control device 9 via a connector CN1 (FIG. 1), and has the other end detachably connected to the camera head 5 via a connector CN2 (FIG. 1). The first transmission cable 6 transmits the image signal output from the camera head 5 to the control device 9, and transmits the control signal, synchronization signal, clock, power, or the like output from the control device 9 individually to the camera head 5. Note that the image signal or the like transmitted from the camera head 5 to the control device 9 via the first transmission cable 6 may be transmitted in an optical signal or in an electrical signal. The same applies to transmission of control signals, synchronization signals, and clocks from the control device 9 to the camera head 5 via the first transmission cable 6.

The display device 7 is implemented by a display using liquid crystal, organic electro luminescence (EL), or the like, and displays an image based on a video signal from the control device 9 under the control of the control device 9.

The second transmission cable 8 has one end detachably connected to the display device 7 and the other end detachably connected to the control device 9. The second transmission cable 8 transmits the video signal processed by the control device 9 to the display device 7.

The control device 9 corresponds to the image processing apparatus according to the first embodiment. The control device 9 includes a central processing unit (CPU) or the like, and comprehensively controls operation of the light source device 3, the camera head 5, and the display device 7. The detailed configuration of the control device 9 will be described below.

The third transmission cable 10 has one end detachably connected to the light source device 3 and the other end detachably connected to the control device 9. The third transmission cable 10 transmits a control signal from the control device 9 to the light source device 3.

Configuration of Control Device

Figure 2:
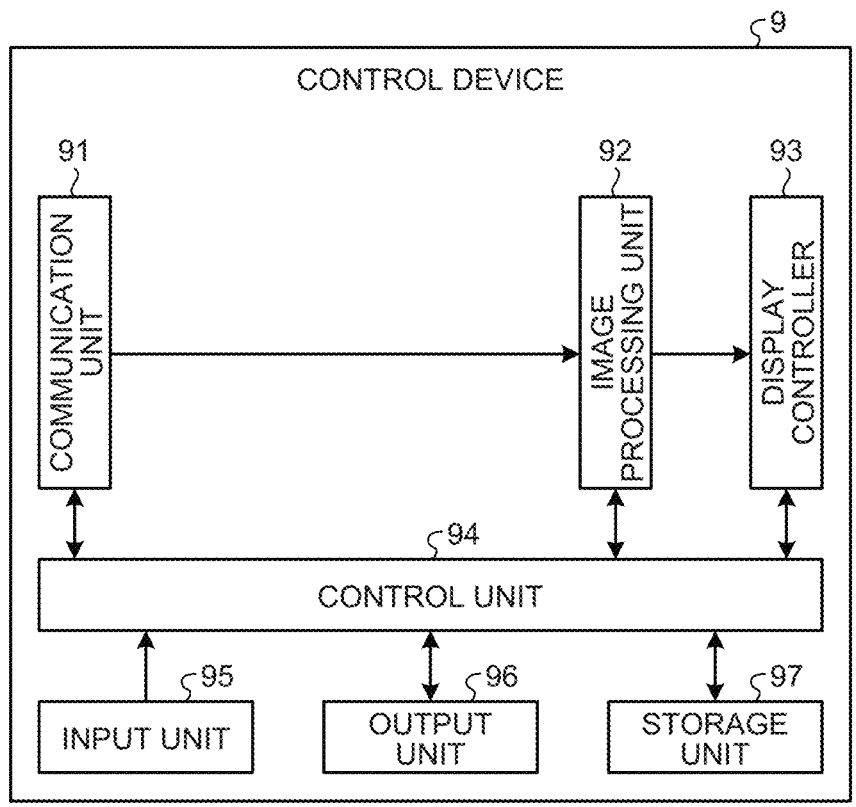
FIG. 2 is a block diagram illustrating a configuration of a control device.

Next, the configuration of the control device 9 will be described with reference to FIG. 2. FIG. 2 is a block diagram illustrating a configuration of the control device 9. As illustrated in FIG. 2, the control device 9 includes a communication unit 91, an image processing unit 92, a display controller 93, a control unit 94, an input unit 95, an output unit 96, and a storage unit 97.

The communication unit 91 functions as a receiver that receives an image signal (RAW signal (digital signal)) output from the camera head 5 via the first transmission cable 6. For example, the communication unit 91 includes a high-speed serial interface that performs image signal communication with the camera head 5 at a transmission rate of 1 Gbps or more.

Under the control of the control unit 94, the image processing unit 92 performs image processing on an image signal (RAW signal (digital signal)) output from the camera head 5 and received by the communication unit 91. The detailed configuration of the image processing unit 92 will be described below.

Under the control of the control unit 94, the display controller 93 generates a video signal for display based on image signals (Y, Cb, Cr) that have undergone image processing by the image processing unit 92. Subsequently, the display controller 93 outputs the video signal to the display device 7 via the second transmission cable 8. With this process, the display device 7 displays an image based on the video signal.

The control unit 94 is constituted with a CPU, for example, and outputs a control signal via the first to third transmission cables 6, 8 and 10, thereby controlling operations of the light source device 3, the camera head 5, and the display device 7, as well as controlling entire operation of the control device 9.

The input unit 95 is constituted with an operation device such as a mouse, a keyboard, and a touch panel, and receives user operations performed by a user such as a doctor. Subsequently, the input unit 95 outputs an operation signal corresponding to the user operation to the control unit 94.

The output unit 96 is constituted with a speaker, a printer, or the like, and outputs various types of information.

The storage unit 97 stores a program executed by the control unit 94, information needed for processing performed by the control unit 94, or the like.

Functional Configuration of Image Processing Unit

Figure 3:
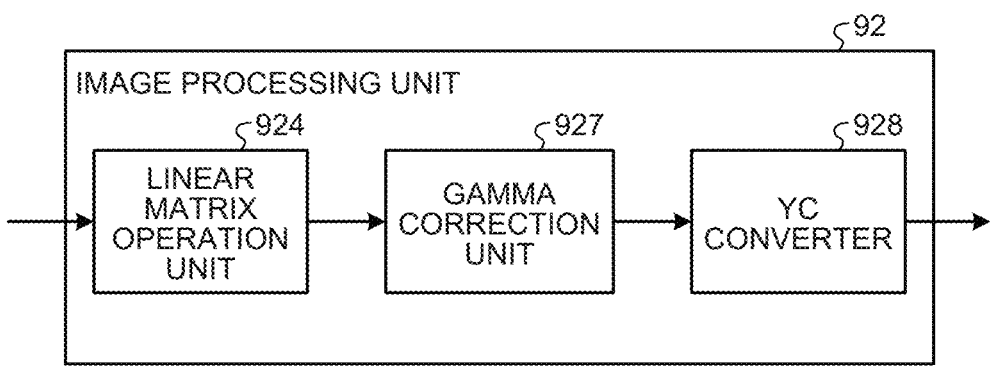
FIG. 3 is a block diagram illustrating a configuration of an image processing unit.

Next, the configuration of the image processing unit 92 will be described with reference to FIG. 3. FIG. 3 is a block diagram illustrating the configuration of the image processing unit 92. As illustrated in FIG. 3, the image processing unit 92 includes a linear matrix operation unit 924, a gamma correction unit 927, and a YC converter 928. The image processing unit 92 may also perform image processing such as white balance adjustment, contour correction process, noise reduction processing for reducing noise components, clamp processing for removing offset components, defect correction processing for correcting defects due to a hot pixel and the like, demosaic processing, and color difference correction processing for the color difference signal.

The linear matrix operation unit 924 has a function of performing a linear matrix operation on an input image signal. Specifically, the linear matrix operation unit 924 sets a matrix coefficient in accordance with the input image signal, and performs a linear matrix operation on the image signal using the set matrix coefficient. The linear matrix operation is an arithmetic operation performed to bring the RGB signals output by the camera head 5 closer to the ideal RGB characteristics and improve the color reproducibility. For example, the linear matrix operation unit 924 performs a linear matrix operation of multiplying RGB image signals input from the camera head 5 via the communication unit 91 by a matrix coefficient. Subsequently, the linear matrix operation unit 924 outputs the image signal after the linear matrix operation, to the gamma correction unit 927. The detailed configuration of the linear matrix operation unit 924 will be described below.

The gamma correction unit 927 has a function of performing gamma correction on the input image signal. For example, the gamma correction unit 927 performs gamma correction of correcting the image signal input from the linear matrix operation unit 924 by using an inverse function of the gamma characteristic of the display device 7. Subsequently, the gamma correction unit 927 outputs the image signal that has undergone the gamma correction to the YC converter 928.

The YC converter 928 has a function of generating a luminance signal (hereinafter, also referred to as "luminance Y") from the input image signal. For example, the YC converter 928 performs conversion processing for converting RGB signals contained in an image signal input from the gamma correction unit 927 into luminance signals. Furthermore, the YC converter 928 has a function of generating a color difference signal from the input image signal. For example, the YC converter 928 performs conversion processing for converting RGB signals contained in an image signal input from the gamma correction unit 927 into color difference signals. Subsequently, the YC converter 928 outputs the generated image signals (Y, Cb, Cr) to the display controller 93.

Configuration of Linear Matrix Operation Unit

Figure 4:
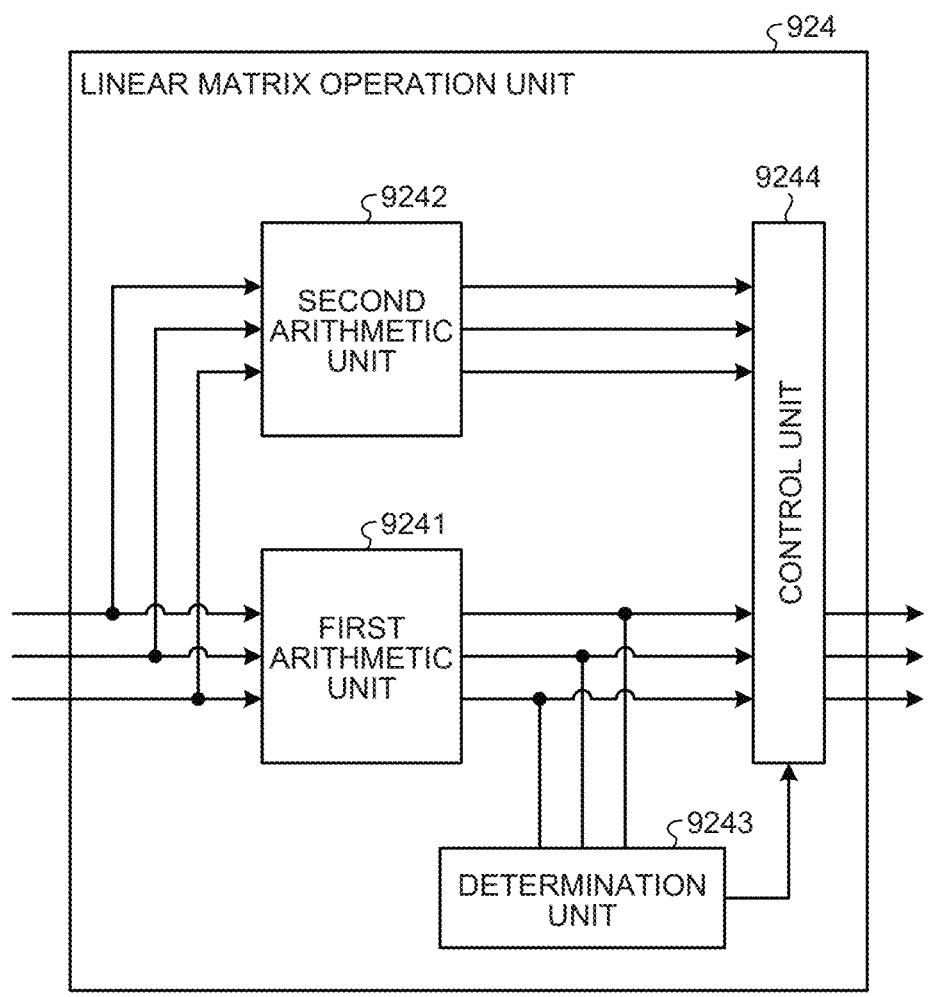
FIG. 4 is a diagram illustrating a configuration of a linear matrix operation unit illustrated in FIG. 3.

Next, the configuration of the linear matrix operation unit 924 will be described with reference to FIG. 4 FIG. 4 is a diagram illustrating a configuration of a linear matrix operation unit illustrated in FIG. 3. As illustrated in FIG. 4, the linear matrix operation unit 924 includes a first arithmetic unit 9241, a second arithmetic unit 9242, a determination unit 9243, and a control unit 9244.

The first arithmetic unit 9241 performs a linear matrix operation on the image signal using a predetermined matrix coefficient. It is preferable that the matrix coefficient of the first arithmetic unit 9241 is set to a value that sufficiently enhances the color reproducibility. In the following Formula (1), $m_{11}$ to $m_{33}$ are linear matrix coefficients. Multiplying the input image signals ($R_{img}$, $G_{img}$, $B_{img}$), which are RGB signals, by the linear matrix coefficients will calculate an operation result ($R_{lmt}$, $G_{lmt}$, $B_{lmt}$)

$$\begin{pmatrix} R_{imt} \\ G_{imt} \\ B_{imt} \end{pmatrix} = \begin{pmatrix} m_{11} & m_{12} & m_{13} \\ m_{21} & m_{22} & m_{23} \\ m_{31} & m_{32} & m_{33} \end{pmatrix} \begin{pmatrix} R_{img} \\ G_{img} \\ B_{img} \end{pmatrix} \quad (1)$$

The second arithmetic unit 9242 performs a linear matrix operation on the image signal using a predetermined matrix coefficient. The matrix coefficient of the second arithmetic unit 9242 is not particularly limited as long as it is a value different from the value for the first arithmetic unit 9241. Still, the matrix coefficient is preferably set to a value that prevents malfunction such as producing negative luminance Y. The matrix coefficient that prevents malfunction is an identity matrix illustrated in the following Formula (2), for example.

$$\begin{pmatrix} 1 & 0 & 0 \\ 0 & 1 & 0 \\ 0 & 0 & 1 \end{pmatrix} \quad (2)$$

When the second arithmetic unit 9242 uses an identity matrix, the operation result would not become a non-existent color, and no malfunction would occur. The second arithmetic unit 9242 may output the input image signal as it is without performing multiplication by the identity matrix. That is, the linear matrix operation unit 924 may output the image signal as it is.

In order to detect a case where the operation result of the arithmetic unit indicates a non-existent color space or a case where the color reproduction deviates from the reality, the determination unit 9243 determines whether the operation result of the arithmetic unit satisfies a predetermined condition. The determination unit 9243 determines, for example, whether the luminance Y calculated by using the operation result of the first arithmetic unit 9241 is negative.

Specifically, the determination unit 9243 determines whether the luminance Y of the image signals (Y, Cb, Cr) generated as a result of output of the operation result of the first arithmetic unit 9241 performed by the linear matrix operation unit 924 and a result of individual operations performed by the gamma correction unit 927 and the YC converter 928, is negative. A calculation example in which the luminance Y is negative will be described below.

The control unit 9244 outputs the operation result of the arithmetic unit (either the first arithmetic unit 9241 or the second arithmetic unit 9242) selected in accordance with the determination result of the determination unit 9243. Specifically, in a case where the determination unit 9243 has determined that the luminance Y calculated by using the operation result of the first arithmetic unit 9241 is not negative, the control unit 9244 outputs the operation result of the first arithmetic unit 9241 to the gamma correction unit 927. In contrast, in a case where the determination unit 9243 has determined that the luminance Y calculated by using the operation result of the first arithmetic unit 9241 is negative, the control unit 9244 outputs the operation result of the second arithmetic unit 9242 to the gamma correction unit 927.

[Calculation Example where Luminance is Negative]

Next, a calculation example in which the luminance Y is negative will be described. First, it is assumed that the matrix coefficient of the first arithmetic unit 9241 includes values illustrated in the following Formula (3).

$$\begin{pmatrix} R_{imt} \\ G_{imt} \\ B_{imt} \end{pmatrix} = \begin{pmatrix} 0.6 & 0.4 & 0 \\ -0.4 & 1.4 & 0 \\ 0 & 0 & 1 \end{pmatrix} \begin{pmatrix} R_{img} \\ G_{img} \\ B_{img} \end{pmatrix} \quad (3)$$

For example, when the input image signals ($R_{img}$, $G_{img}$, $B_{img}$)=(1, 0, 0), the operation result ($R_{lmt}$, $G_{lmt}$, $B_{lmt}$)=(0.6, −0.4, 0) is obtained by the first arithmetic unit 9241.

This operation result ($R_{lmt}$, $G_{lmt}$, $B_{lmt}$) undergoes gamma processing by the gamma correction unit 927 to turn into signals ($R_{gam}$, $G_{gam}$, $B_{gam}$). Gamma processing is expressed as $f_{gam}(\ )$ by the calculation formula specified in the video format recommendation BT. 2020, which is calculated as: $R_{gam}=f_{gam}(R_{lmt})=f_{gam}(0.6)=0.774$, $G_{gam}=f_{gam}(G_{lmt})=f_{gam}(-0.4)=-0.628$. The gamma processing has no regulation for negative inputs. Therefore, when the input is negative, calculation is performed with the inverted sign, and output is performed with re-inverted sign.

Furthermore, using the calculated signals $R_{gam}$, $G_{gam}$, and $B_{gam}$, calculations of Y, Cb, and Cr are performed by the following Formula (4) specified in the video format recommendation BT. 2020.

$$\begin{pmatrix} Y \\ Cb \\ Cr \end{pmatrix} = \begin{pmatrix} 0.2627 & 0.678 & 0.0593 \\ -0.1396 & -0.3604 & 0.5 \\ 0.5 & -0.4598 & -0.0402 \end{pmatrix} \begin{pmatrix} R_{gam} \\ G_{gam} \\ B_{gam} \end{pmatrix} \quad (4)$$

Then, the luminance Y will be negative by the following Formula (5).

$$Y = 0.2627 R_{gam} + 0.678 G_{gam} + 0.0593 B_{gam} \quad (5)$$

-continued $$= 0.2627 \times 0.774 + 0.678 \times (-0.628)$$
$$= -0.222$$

As described above, the luminance Y might be negative in some cases, and in such a case, the determination unit 9243 determines that the luminance Y calculated by using the operation result of the first arithmetic unit 9241 is negative.

Linear Matrix Operation Process

Figure 5:
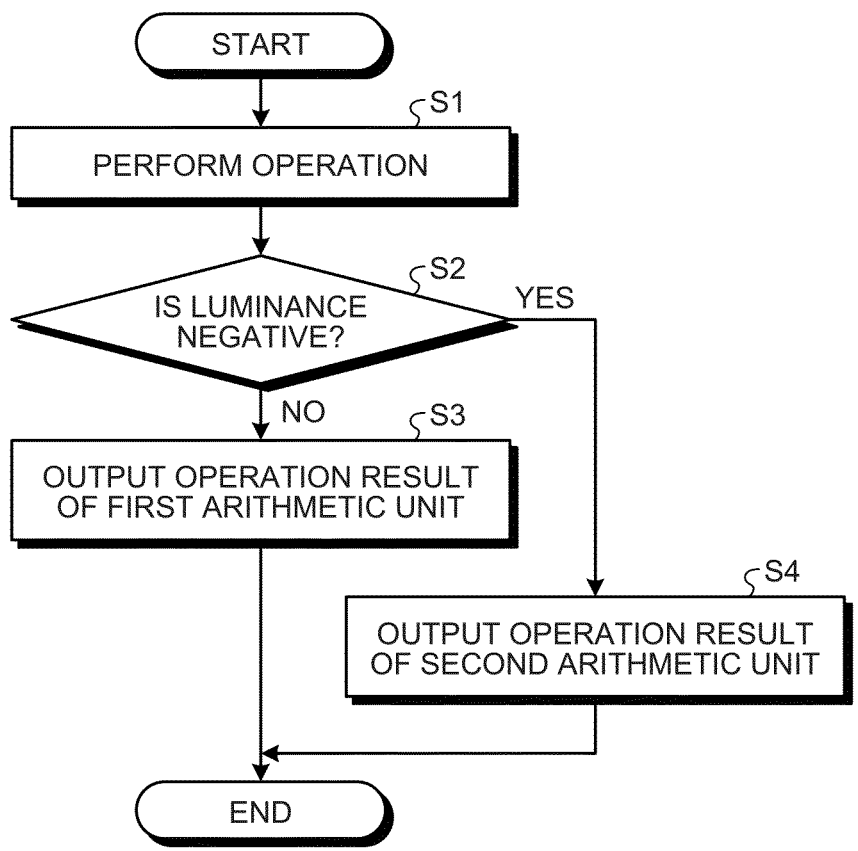
FIG. 5 is a flowchart illustrating an outline of processing executed by the linear matrix operation unit.

FIG. 5 is a flowchart illustrating an outline of processing executed by the linear matrix operation unit. As illustrated in FIG. 5, the first arithmetic unit 9241 and the second arithmetic unit 9242 first perform a matrix operation of multiplying the input image signals, which are RGB signals, by a matrix coefficient (step S1).

Subsequently, the determination unit 9243 determines whether the luminance Y calculated by using the operation result of the first arithmetic unit 9241 is negative (step S2).

In a case where the determination unit 9243 has determined that the luminance Y calculated by using the operation result of the first arithmetic unit 9241 is not negative (step S2: No), the control unit 9244 outputs the operation result of the first arithmetic unit 9241 to the gamma correction unit 927 (step S3).

In contrast, in a case where the determination unit 9243 has determined that the luminance Y calculated by using the operation result of the first arithmetic unit 9241 is negative (step S2: Yes), the control unit 9244 outputs the operation result of the second arithmetic unit 9242 to the gamma correction unit 927 (step S4).

According to the first embodiment described above, when the luminance Y calculated by using the operation result of the first arithmetic unit 9241 is not negative, the operation result of the first arithmetic unit 9241 will be output to the gamma correction unit 927, leading to sufficiently good color reproducibility. When the luminance Y calculated by using the operation result of the first arithmetic unit 9241 is negative, the operation result of the second arithmetic unit 9242 will be output to the gamma correction unit 927, making it possible to prevent a malfunction of having a negative luminance Y.

In step S2 of FIG. 5, the determination unit 9243 determines whether the luminance Y is negative. Alternatively, however, determination may be performed as to whether the operation result ($R_{lmt}1$, $G_{lmt}1$, $B_{lmt}1$) of the first arithmetic unit 9241 satisfies $R_{lmt}1 > R_{max} \times \delta1$, $G_{lmt}1 > G_{max} \times \delta1$, and $B_{lmt}1 > B_{max} \times \delta1$. Incidentally, $R_{max}$, $G_{max}$, and $B_{max}$ are the maximum values in the image signals of colors (red, green, and blue), respectively. For example, with the color depth of 10 bits, the image signal input to the linear matrix operation unit 924 is in a range of 0 to 1023, and thus, the maximum values $R_{max}$, $G_{max}$, and $B_{max}$ are all 1023. Furthermore, $\delta1$ is a ratio, and is set to 0.8 to 0.95, for example.

Furthermore, in step S2 of FIG. 5, the determination unit 9243 may determine whether the operation results ($R_{lmt}1$, $G_{lmt}1$, $B_{lmt}1$) of the first arithmetic unit 9241 satisfy $R_{lmt}1 < R_{max} \times \delta2$, $G_{lmt}1 < G_{max} \times \delta2$, and $B_{lmt}1 < B_{max} \times \delta2$, respectively. Note that $\delta2$ is a ratio, and is set to 0.05 to 0.2, for example.

Furthermore, in step S2 of FIG. 5, in a case where the determination unit 9243 has determined that the results do not satisfy $R_{lmt}1 > R_{max} \times \delta1$, $G_{lmt}1 > G_{max} \times \delta1$, and $B_{lmt}1 > B_{max} \times \delta1$, and do not satisfy $R_{lmt}1 < R_{max} \times \delta2$, $G_{lmt}1 < G_{max} \times \delta2$, and $B_{lmt}1 < B_{max} \times \delta2$ (step S2: No), the control unit 9244 outputs the operation result of the first arithmetic unit 9241 to the gamma correction unit 927 (step S3). In contrast, in a case where the determination unit 9243 has determined that the results satisfy $R_{lmt}1 > R_{max} \times \delta1$, $G_{lmt}1 > G_{max} \times \delta1$, and $B_{lmt}1 > B_{max} \times \delta1$, or satisfy $R_{lmt}1 < R_{max} \times \delta2$, $G_{lmt}1 < G_{max} \times \delta2$, and $B_{lmt}1 < B_{max} \times \delta2$ (step S2: Yes), the control unit 9244 outputs the operation result of the second arithmetic unit 9242 to the gamma correction unit 927 (step S4). This processing makes it possible to prevent unnecessary coloring for either a dark subject or a bright subject.

Furthermore, in step S2 of FIG. 5, the determination unit 9243 determines whether the luminance Y is negative. Alternatively, it is allowable to determine whether the luminance Y and the color difference signals Cr and Cb satisfy predetermined conditions. Specifically, the determination unit 9243 may determine whether $\varepsilon1 \times Y_{max} < Y < \varepsilon2 \times Y_{max}$, $Cb > \varepsilon3 \times Cb_{max}$, and $\varepsilon4 \times Cr_{max} < Cr < \varepsilon5 \times Cr_{max}$ are individually satisfied. Note that $Y_{max}$ is the maximum value of the luminance Y. For example, with the bit depth of 10 bits, the luminance Y is in a range of 0 to 1023, and thus, $Y_{max}$ is 1023. In addition, $Cb_{max}$ is the maximum value of the color difference signal Cb. For example, with the bit depth of 10 bits, the color difference signal Cb is in a range of −512 to +511, and thus, $Cb_{max}$ is +511. $Cr_{max}$ is the maximum value of the color difference signal Cr. For example, with the bit depth of 10 bits, the color difference signal Cb is in a range of −512 to +511, and thus, $Cr_{max}$ is +511. Furthermore, ε1, ε2, ε3, ε4, and ε5 are ratios, and exemplary settings of these are: ε1=0.5, ε2=0.6, ε3=0.8, ε4=−0.2, and ε5=0.2.

In a case where the determination unit 9243 has determined that $\varepsilon1 \times Y_{max} < Y < \varepsilon2 \times Y_{max}$, $Cb > \varepsilon3 \times Cb_{max}$, and $\varepsilon4 \times Cr_{max} < Cr < \varepsilon5 \times Cr_{max}$ are not satisfied (step S2: No), the control unit 9244 outputs the operation result of the first arithmetic unit 9241 to the gamma correction unit 927 (step S3). In contrast, in a case where the determination unit 9243 has determined that $\varepsilon1 \times Y_{max} < Y < \varepsilon2 \times Y_{max}$, $Cb > \varepsilon3 \times Cb_{max}$, and $\varepsilon4 \times Cr_{max} < Cr < \varepsilon5 \times Cr_{max}$ are satisfied (step S2: Yes), the control unit 9244 outputs the operation result of the second arithmetic unit 9242 to the gamma correction unit 927 (step S4). With this processing, it is possible to reduce the deterioration of the reproduction of a specific color, if any.

Second Embodiment

In the image processing apparatus according to a second embodiment, the configuration other than the linear matrix operation unit is similar to the configuration of the first embodiment, and thus the description thereof will be omitted.

Configuration of Linear Matrix Operation Unit

Figure 6:
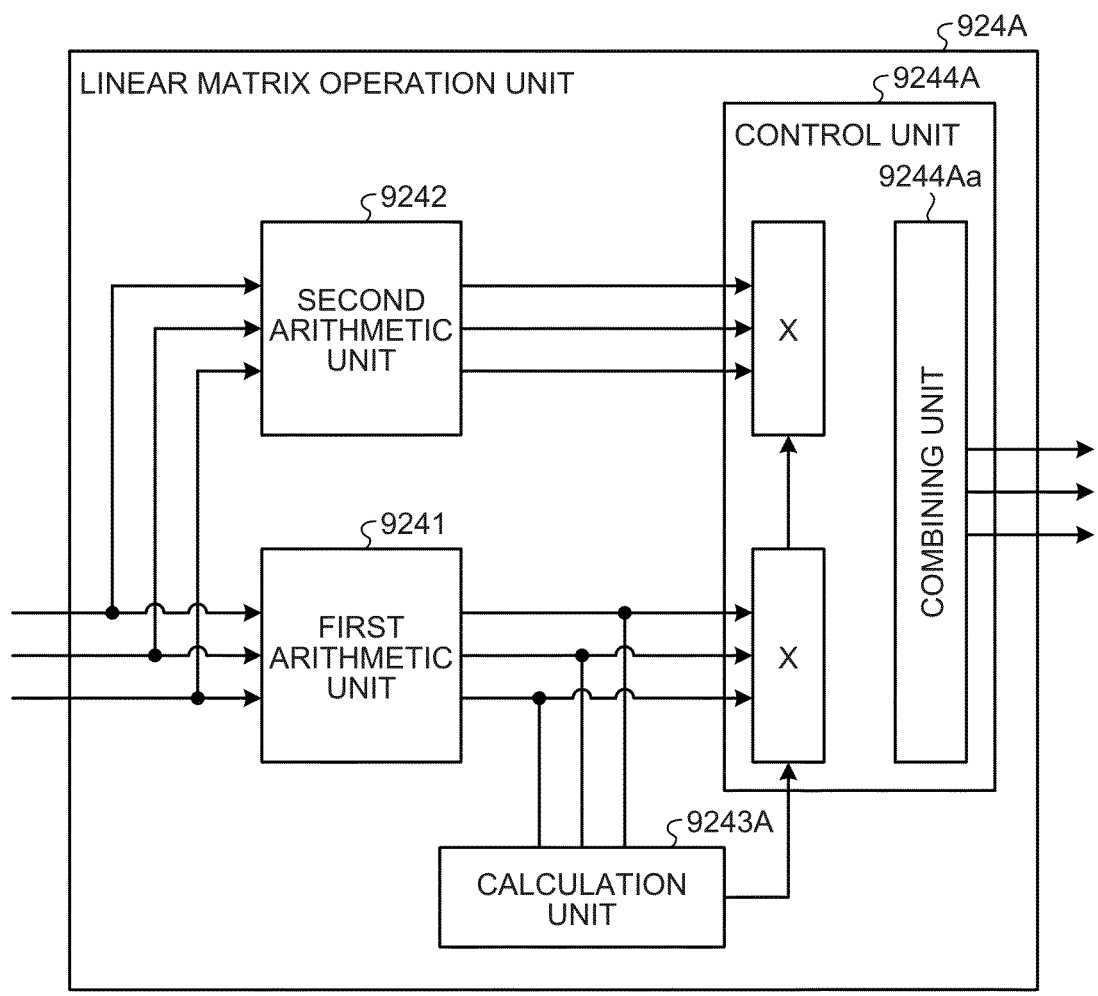
FIG. 6 is a diagram illustrating a configuration of a linear matrix operation unit in an image processing apparatus according to a second embodiment.

FIG. 6 is a diagram illustrating a configuration of a linear matrix operation unit in the image processing apparatus according to the second embodiment. As illustrated in FIG. 6, a linear matrix operation unit 924A includes a calculation unit 9243A and a control unit 9244A. A same reference sign will be given to the configuration similar to the configuration of the first embodiment, and description thereof will be omitted.

The calculation unit 9243A calculates the ratio for combining the arithmetic operation results of the arithmetic unit in accordance with the arithmetic operation results of the arithmetic unit. The calculation unit 9243A calculates the ratio for combining the operation results of the arithmetic unit in accordance with the luminance Y calculated by using the arithmetic operation result of the first arithmetic unit 9241. Specifically, the calculation unit 9243A calculates the ratio for combining the arithmetic operation result of the arithmetic unit in accordance with the luminance Y of the image signals (Y, Cb, Cr) generated as a result of output of the operation result of the first arithmetic unit 9241 performed by the linear matrix operation unit 924A and a result of individual arithmetic operations performed by the gamma correction unit 927 and the YC converter 928. When the luminance Y is negative, the calculation unit 9243A calculates the ratio of the second arithmetic unit 9242 as 100%. Furthermore, when the luminance Y is zero or more, the calculation unit 9243A calculates the ratio to be combined so that the larger the luminance Y, the larger the ratio of the first arithmetic unit 9241.

The control unit 9244A combines and outputs the operation results of the arithmetic units (first arithmetic unit 9241 and second arithmetic unit 9242) based on the ratio calculated by the calculation unit 9243A.

The control unit 9244A includes a combining unit 9244Aa. The combining unit 9244Aa combines the operation results of the first arithmetic unit 9241 and the second arithmetic unit 9242. For example, when the ratio of the first arithmetic unit 9241 is 80%, the ratio of the second arithmetic unit 9242 is 20%, and in a case where the operation results of the first arithmetic unit 9241 ($R_{lmt}1$, $G_{lmt}1$, $B_{lmt}1$) and the operation results of the second arithmetic unit 9242 ($R_{lmt}2$, $G_{lmt}2$, $B_{lmt}2$) have been input, the combining unit 9244Aa will output combining results ($R_{lmt}3$, $G_{lmt}3$, $B_{lmt}3$)=($0.8 \times R_{lmt}1 + 0.2 \times R_{lmt}2$, $0.8 \times G_{lmt}1 + 0.2 \times G_{lmt}2$, $0.8 \times B_{lmt}1 + 0.2 \times B_{lmt}2$) to the gamma correction unit 927.

Linear Matrix Operation Process

Figure 7:
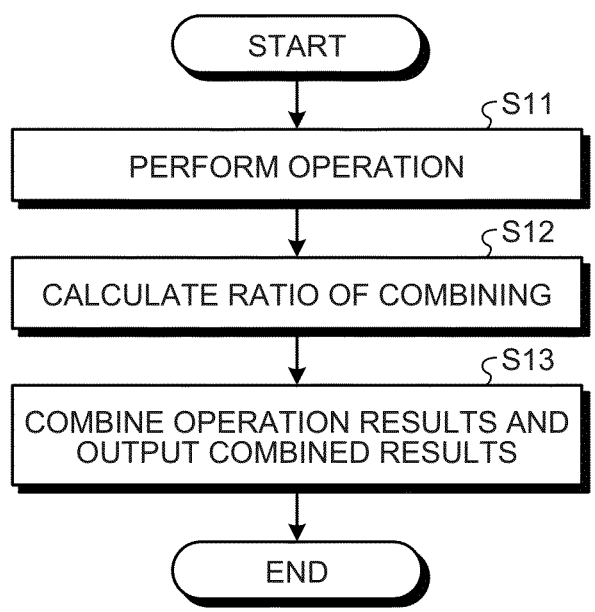
FIG. 7 is a flowchart illustrating an outline of processing executed by the linear matrix operation unit.

FIG. 7 is a flowchart illustrating an outline of the processing executed by the linear matrix operation unit. As illustrated in FIG. 7, the first arithmetic unit 9241 and the second arithmetic unit 9242 first perform a matrix operation of multiplying the input image signals, which are RGB signals, by a matrix coefficient (step S11).

Subsequently, the calculation unit 9243A calculates the ratio for combining the operation results of the arithmetic unit in accordance with the luminance Y calculated by using the arithmetic operation result of the first arithmetic unit 9241 (step S12).

Thereafter, the control unit 9244A combines the operation results of the first arithmetic unit 9241 and the second arithmetic unit 9242 based on the ratio calculated by the calculation unit 9243A, and outputs the combined result to the gamma correction unit 927 (step S13).

According to the second embodiment described above, in a case where the luminance Y calculated by using the operation result of the first arithmetic unit 9241 is zero or more, the greater the luminance Y, the larger the ratio of the first arithmetic unit 9241 will be set. This makes it possible to achieve color transition smoothly to enable natural expression of the colors, leading to further improvement of the color reproducibility. Furthermore, according to the second embodiment, when the luminance Y calculated by using the operation result of the first arithmetic unit 9241 is negative, the operation result will be output using the ratio 100% of the second arithmetic unit 9242, making it possible to prevent an occurrence of malfunction of producing negative luminance Y.

Third Embodiment

In the image processing apparatus according to a third embodiment, the configuration other than the linear matrix operation unit is similar to the configuration of the first embodiment, and thus the description thereof will be omitted.

Configuration of Linear Matrix Operation Unit

Figure 8:
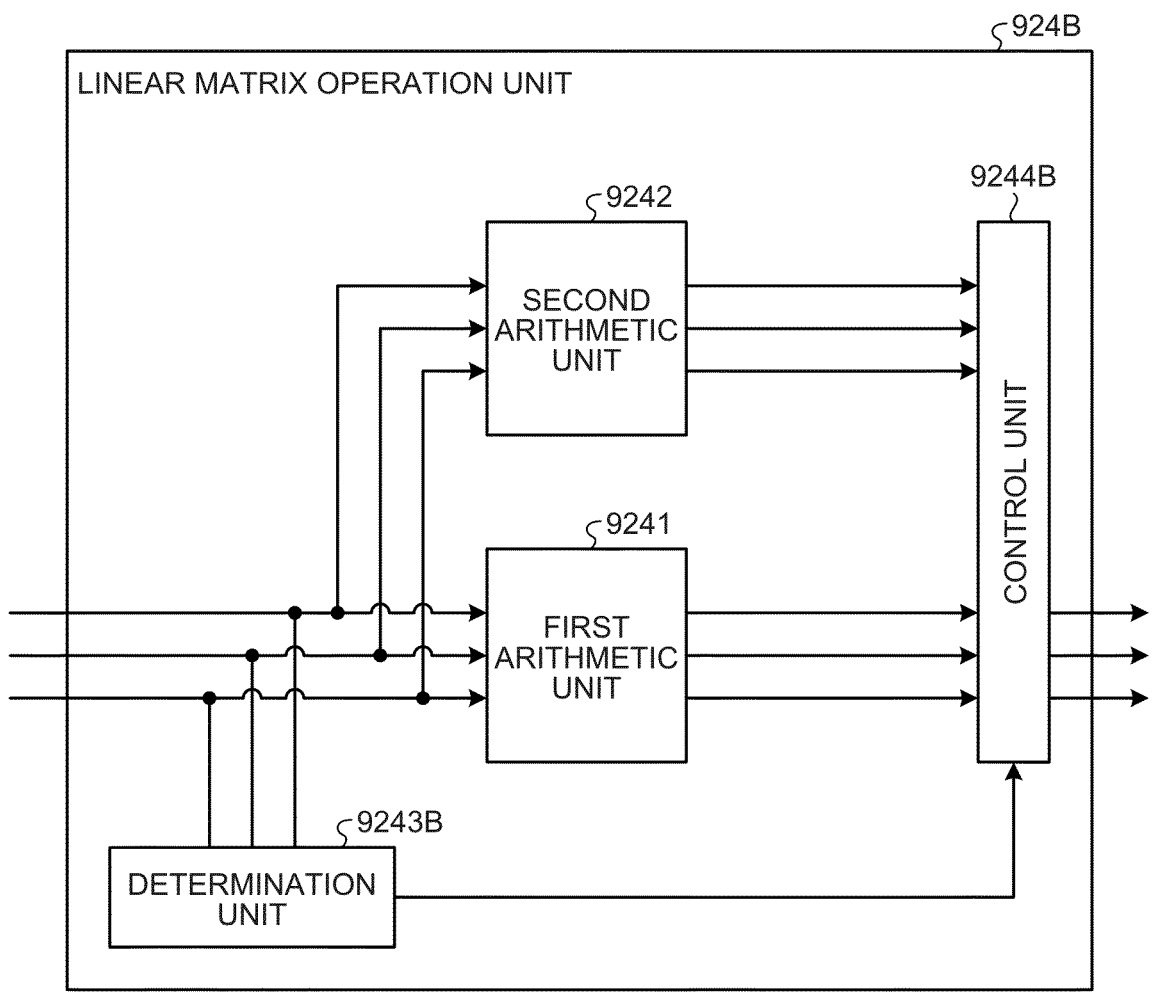
FIG. 8 is a diagram illustrating a configuration of a linear matrix operation unit in an image processing apparatus according to a third embodiment.

FIG. 8 is a diagram illustrating a configuration of a linear matrix operation unit in an image processing apparatus according to the third embodiment. As illustrated in FIG. 8, a linear matrix operation unit 924B includes a determination unit 9243B and a control unit 9244B. A same reference sign will be given to the configuration similar to the configuration of the first embodiment, and description thereof will be omitted.

The determination unit 9243B determines whether an image signal satisfies a predetermined condition. The determination unit 9243B determines whether the luminance Y calculated by using the operation result in a case where the image signal has been input to the first arithmetic unit 9241, is negative, for example. As a result, the determination unit 9243B detects an image signal having a negative luminance Y in advance. Note that an image signal having a negative luminance Y may be calculated in advance by using the matrix coefficient of the first arithmetic unit 9241. With this calculation result stored in the storage unit 97 as a table, the determination unit 9243B may make a determination by referring to this table.

The control unit 9244B outputs the operation result of the arithmetic unit (either the first arithmetic unit 9241 or the second arithmetic unit 9242) selected in accordance with the determination result of the determination unit 9243B. Specifically, when the determination unit 9243B has determined that the luminance Y calculated by using the operation result in a case where the image signal has been input to the first arithmetic unit 9241 is not negative, the control unit 9244B outputs the operation result of the first arithmetic unit 9241 to the gamma correction unit 927. In contrast, when the determination unit 9243B has determined that the luminance Y calculated by using the operation result in a case where the image signal has been input to the first arithmetic unit 9241 is negative, the control unit 9244B outputs the operation result of the second arithmetic unit 9242 to the gamma correction unit 927.

Linear Matrix Operation Process

Figure 9:
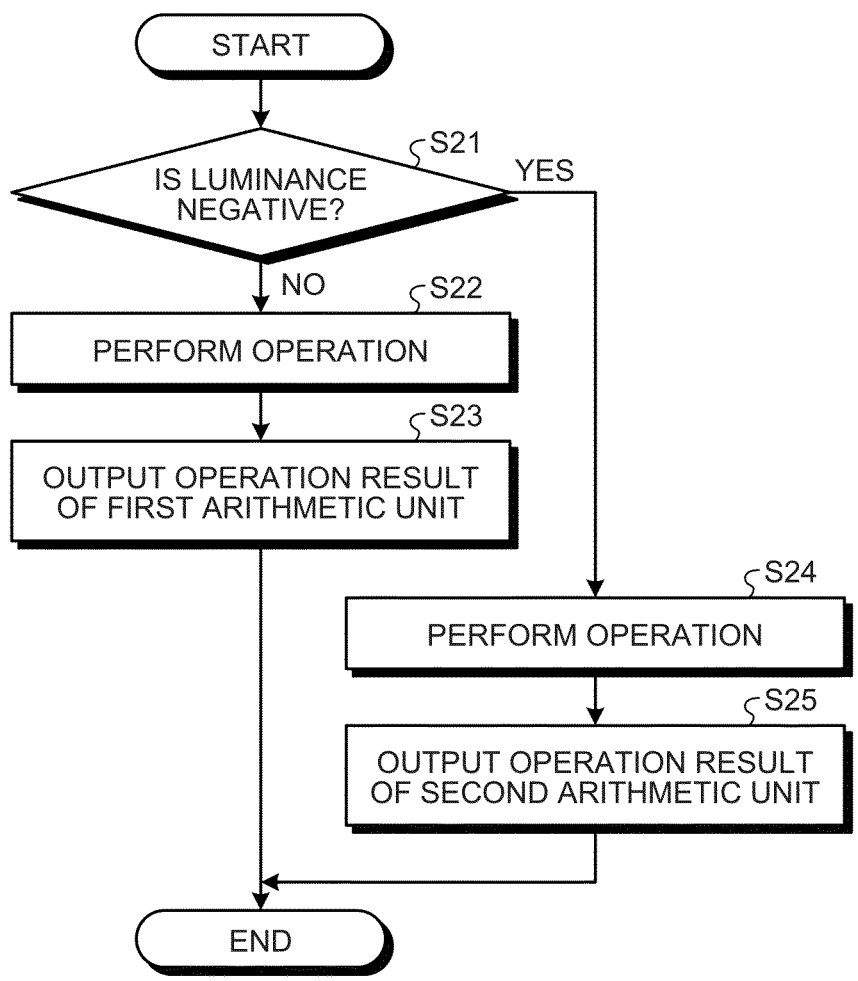
FIG. 9 is a flowchart illustrating an outline of processing executed by the linear matrix operation unit.

FIG. 9 is a flowchart illustrating an outline of the processing executed by the linear matrix operation unit. As illustrated in FIG. 9, the determination unit 9243B determines whether the luminance Y calculated by using the operation result in a case where the image signal has been input to the first arithmetic unit 9241, is negative (step S21).

When the determination unit 9243B has determined that the luminance Y calculated by using the operation result in a case where the image signal has been input to the first arithmetic unit 9241 is not negative (step S21: No), the first arithmetic unit 9241 performs matrix operation of multiplying the input image signals, which are RGB signals, by a matrix coefficient (step S22).

Thereafter, the control unit 9244B outputs the operation result of the first arithmetic unit 9241 to the gamma correction unit 927 (step S23).

In a case where the determination unit 9243B has determined in step S21 that the luminance Y calculated by using the operation result in a case where the image signal has been input to the first arithmetic unit 9241 is negative (step S21: Yes), the second arithmetic unit 9242 performs matrix operation of multiplying the input image signals, which are RGB signals, by a matrix coefficient (step S24).

Thereafter, the control unit 9244B outputs the operation result of the second arithmetic unit 9242 to the gamma correction unit 927 (step S25).

According to the third embodiment described above, when the luminance Y calculated by using the operation result in the case where the image signal has been input to the first arithmetic unit 9241 is not negative, the operation result of the first arithmetic unit 9241 will be output to the gamma correction unit 927, leading to sufficiently good color reproducibility. When the luminance Y calculated by using the operation result at the time of input of the image signal into the first arithmetic unit 9241 is negative, the operation result of the second arithmetic unit 9242 will be output to the gamma correction unit 927, making it possible to prevent a malfunction of having a negative luminance Y.

In step S21 of FIG. 9, the determination unit 9243B determines whether the luminance Y becomes negative.

Alternatively, however, as illustrated in the first embodiment, it is allowable to determine whether $R_{lmt}1 > R_{max} \times \delta 1$, $G_{lmt}1 > G_{max} \times \delta 1$, and $B_{lmt}1 > B_{max} \times \delta 1$ are satisfied, or allowable to determine whether $R_{lmt}1 < R_{max} \times \delta 2$, $G_{lmt}1 < G_{max} \times \delta 2$, and $B_{lmt}1 < B_{max} \times \delta 2$ are satisfied. Moreover, the determination unit 9243B may determine whether $\varepsilon 1 \times Y_{max} < Y < \varepsilon 2 \times Y_{max}$, $Cb > \varepsilon 3 \times Cb_{max}$, and $\varepsilon 4 \times Cr_{max} < Cr < \varepsilon 5 \times Cr_{max}$ are individually satisfied.

As illustrated in the third embodiment, the image signal input to the arithmetic unit may be used to determine which arithmetic unit to output the operation result. Similarly, even when the control unit has a combining unit as in the second embodiment, the ratio for combining the operation results of the arithmetic unit may be calculated using the image signal input to the arithmetic unit.

Fourth Embodiment

In the image processing apparatus according to a fourth embodiment, the configuration other than the linear matrix operation unit is similar to the configuration of the first embodiment, and thus the description thereof will be omitted.

Configuration of Linear Matrix Operation Unit

Figure 10:
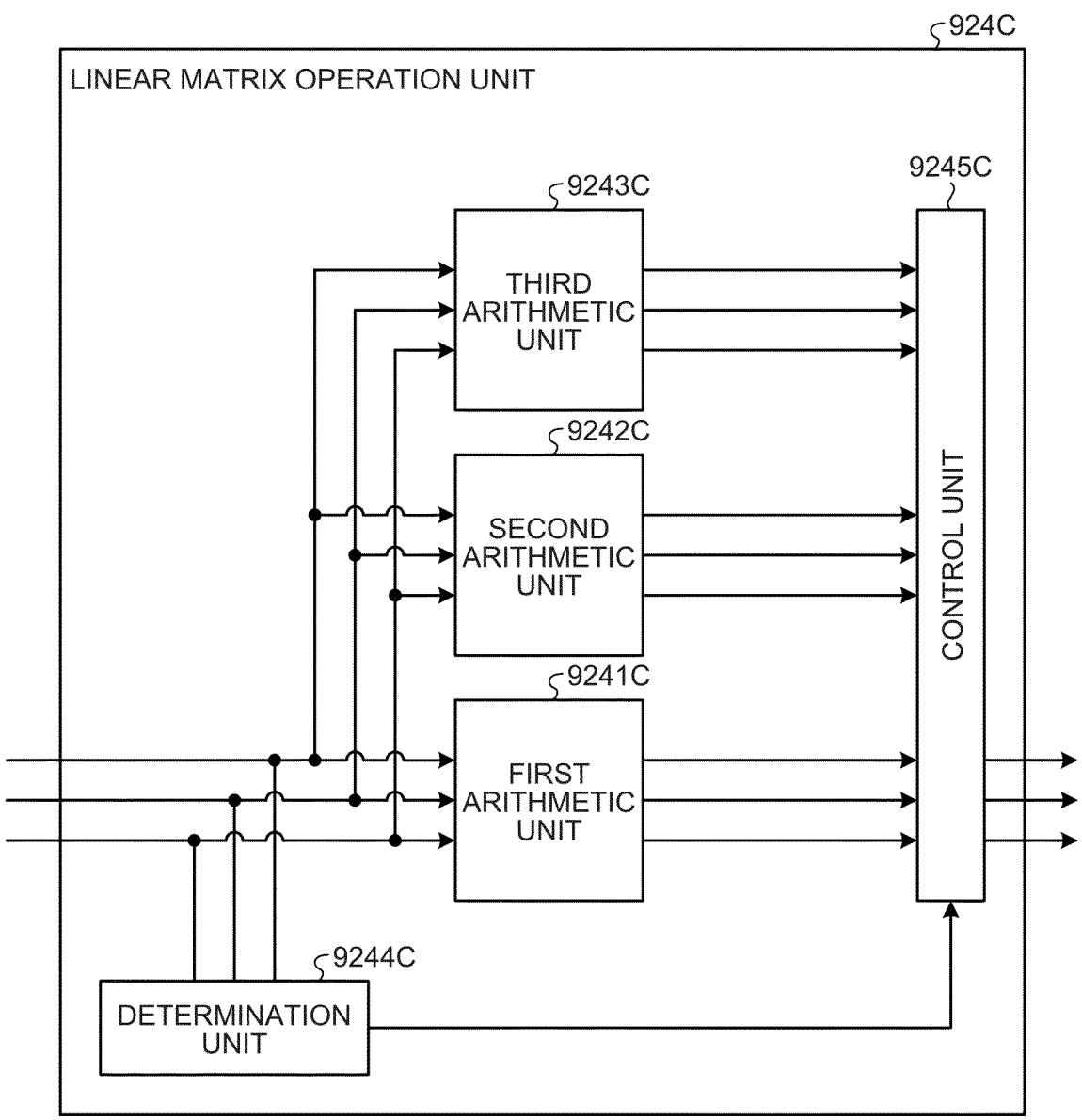
FIG. 10 is a diagram illustrating a configuration of a linear matrix operation unit in an image processing apparatus according to a fourth embodiment.

FIG. 10 is a diagram illustrating a configuration of a linear matrix operation unit in an image processing apparatus according to the fourth embodiment. As illustrated in FIG. 10, a linear matrix operation unit 924C includes a first arithmetic unit 9241C, a second arithmetic unit 9242C, a third arithmetic unit 9243C, a determination unit 9244C, and a control unit 9245C.

The first arithmetic unit 9241C performs a linear matrix operation on an image signal using a predetermined matrix coefficient. The matrix coefficient of the first arithmetic unit 9241C is set to a coefficient optimized for red, for example. In the following, the color optimized by the first arithmetic unit 9241C will be referred to as a first color ($R_{mtx}1$, $G_{mtx}11$, $B_{mtx}1$).

The second arithmetic unit 9242C performs a linear matrix operation on an image signal using a predetermined matrix coefficient. The matrix coefficient of the second arithmetic unit 9242C is set to a coefficient optimized for blue, for example. In the following, the color optimized by the second arithmetic unit 9242C will be referred to as a second color ($R_{mtx}2$, $G_{mtx}2$, $B_{mtx}2$).

The third arithmetic unit 9243C performs a linear matrix operation on an image signal using a predetermined matrix coefficient. The matrix coefficient of the third arithmetic unit 9243C is set to a coefficient optimized for a color other than red and blue, for example. However, the matrix coefficient of the third arithmetic unit 9243C may be in the form of an identity matrix.

The determination unit 9244C determines whether an image signal satisfies a predetermined condition. For example, the determination unit 9244C determines whether the input image signals ($R_{img}$, $G_{img}$, $B_{img}$) satisfy $R_{img} \approx R_{mtx}1$, $G_{img} \approx G_{mtx}1$, and $B_{img} \approx B_{mtx}1$, or satisfy $R_{img} \approx R_{mtx}2$, $G_{img} \approx G_{mtx}2$, and $B_{img} \approx B_{mtx}2$. In addition, the determination unit 9244C may handle the first color ($R_{mtx}1$, $G_{mtx}1$, $B_{mtx}1$), the second color ($R_{mtx}2$, $G_{mtx}2$, $B_{mtx}2$), and the image signal ($R_{img}$, $G_{img}$, $B_{img}$) as vectors, and may determine whether a distance L1 between the first color ($R_{mtx}1$, $G_{mtx}1$, $B_{mtx}1$) and the image signal ($R_{img}$, $G_{img}$, $B_{img}$) and a distance L2 between the second color ($R_{mtx}2$, $G_{mtx}2$, $B_{mtx}2$) and the image signal ($R_{img}$, $G_{img}$, $B_{img}$) are individually predetermined thresholds or less. This distance L1 is calculated by $L1=\sqrt{((R_{mtx}1-R_{img})^2+(G_{mtx}1-G_{img}))^2+(B_{mtx}1-B_{img})^2)}$, while the distance L2 is calculated by $L2=\sqrt{((R_{mtx}2-R_{img})^2+(G_{mtx}2-G_{img})^2+(B_{mtx}2-B_{img})^2)}$. By determining whether the distance L1 or the distance L2 is a predetermined threshold or less, it is possible to determine whether the color is relatively close to the first color optimized by the first arithmetic unit 9241C or to the second color optimized by the second arithmetic unit 9242C.

The control unit 9245C outputs an operation result of the arithmetic unit (either one of the first arithmetic unit 9241C, the second arithmetic unit 9242C, or the third arithmetic unit 9243C) selected in accordance with the determination result of the determination unit 9244C. Specifically, when the determination unit 9244C has determined that the input image signals ($R_{img}$, $G_{img}$, $B_{img}$) satisfy $R_{img} \approx R_{mtx}1$, $G_{img} \approx G_{mtx}1$, and $B_{img} \approx B_{mtx}1$, the control unit 9245C outputs the operation result of the first arithmetic unit 9241C to the gamma correction unit 927. Furthermore, when the determination unit 9244C has determined that the input image signals ($R_{img}$, $G_{img}$, $B_{img}$) satisfy $R_{img} \approx R_{mtx}2$, $G_{img} \approx G_{mtx}2$, $B_{img} \approx B_{mtx}2$, the control unit 9245C outputs the operation result of the second arithmetic unit 9242C to the gamma correction unit 927. Furthermore, when the determination unit 9244C has determined that the input image signals ($R_{img}$, $G_{img}$, $B_{img}$) satisfy neither $R_{img} \approx R_{mtx}1$, $G_{img} \approx G_{mtx}1$, $B_{img} \approx B_{mtx}1$, nor $R_{img} \approx R_{mtx}2$, $G_{img} \approx G_{mtx}2$, $B_{img} \approx B_{mtx}2$, the control unit 9245C outputs the operation result of the third arithmetic unit 9243C to the gamma correction unit 927. Furthermore, the control unit 9245C may output the operation result of the first arithmetic unit 9241C to the gamma correction unit 927 when the distance L1 is a predetermined threshold or less; it may output the operation result of the second arithmetic unit 9242C to the gamma correction unit 927 when the distance L2 is a predetermined threshold or less; and it may output the operation result of the third arithmetic unit 9243C to the gamma correction unit 927 when both the distance L1 and the distance L2 are individually greater than predetermined thresholds.

Linear Matrix Operation Process

Figure 11:
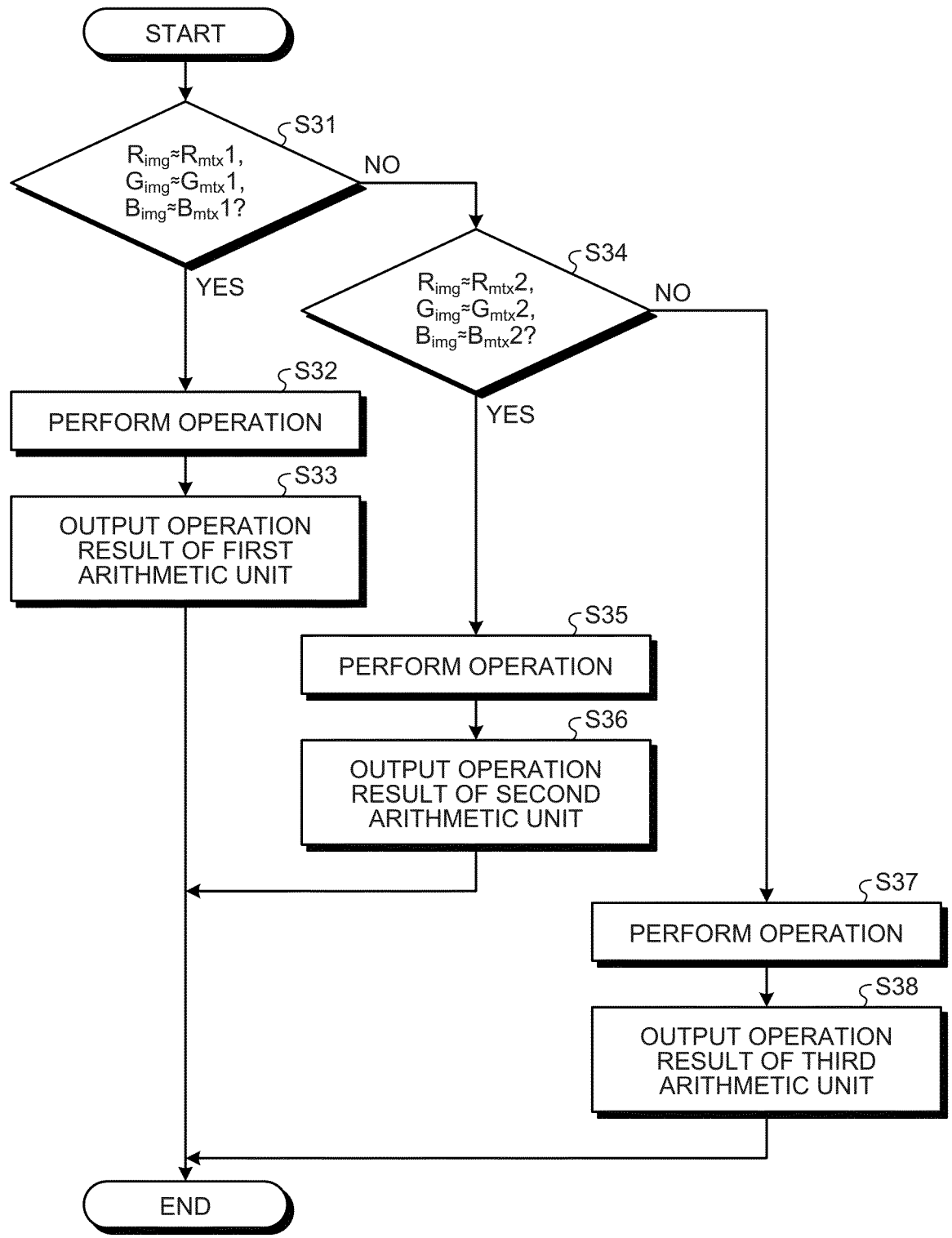
FIG. 11 is a flowchart illustrating an outline of processing executed by the linear matrix operation unit.

FIG. 11 is a flowchart illustrating an outline of the processing executed by the linear matrix operation unit. As illustrated in FIG. 11, the determination unit 9244C determines whether the input image signals ($R_{img}$, $G_{img}$, $B_{img}$) satisfy $R_{img} \approx R_{mtx}1$, $G_{img} G_{mtx}1$, $B_{img} \approx B_{mtx}1$ (step S31). The determination unit 9244C may determine whether the distance L1 is a first threshold $T_o1$ or less. Specifically, the determination unit 9244C determines that $R_{img} \approx R_{mtx}1$, $G_{img} \approx G_{mtx}1$, $B_{img} \approx B_{mtx}1$ are satisfied when the distance L1 is the first threshold $T_o1$ or less, and determines that $R_{img} \approx R_{mtx}1$, $G_{img} \approx G_{mtx}1$, $B_{img} \approx B_{mtx}1$ are not satisfied when the distance L1 is greater than the first threshold $T_o1$.

When the determination unit 9244C has determined that the input image signals ($R_{img}$, $G_{img}$, $B_{img}$) satisfy $R_{img} \approx R_{mtx}1$, $G_{img} \approx G_{mtx}1$, and $B_{img} \approx B_{mtx}1$ (step S31: Yes), the first arithmetic unit 9241C performs a matrix operation of multiplying the input image signals, which are RGB signals, by a matrix coefficient (step S32).

Thereafter, the control unit 9245C outputs the operation result of the first arithmetic unit 9241C to the gamma correction unit 927 (step S33).

In step S31, when the determination unit 9244C has determined that the input image signals ($R_{img}$, $G_{img}$, $B_{img}$) do not satisfy $R_{img} \approx R_{mtx}1$, $G_{img} \approx G_{mtx}1$, and $B_{img} \approx B_{mtx}1$ (step S31: No), the determination unit 9244C determines whether the input image signals ($R_{img}$, $G_{img}$, $B_{img}$) satisfy $R_{img} \approx R_{mtx}2$, $G_{img} \approx G_{mtx}2$, and $B_{img} \approx B_{mtx}2$ (step S34). The determination unit 9244C may determine whether the distance L2 is a second threshold $T_o2$ or less. Specifically, the determination unit 9244C determines that $R_{img} \approx R_{mtx}2$, $G_{img} \approx G_{mtx}2$, and $B_{img} \approx B_{mtx}2$ are satisfied when the distance L2 is the second threshold $T_o2$ or less, and determines that $R_{img} \approx R_{mtx}2$, $G_{img} \approx G_{mtx}2$, and $B_{img} \approx B_{mtx}2$ are not satisfied when the distance L2 is greater than the second threshold $T_o2$.

When the determination unit 9244C has determined that the input image signals ($R_{img}$, $G_{img}$, $B_{img}$) satisfy $R_{img} \approx R_{mtx}2$, $G_{img} \approx G_{mtx}2$, and $B_{img} \approx B_{mtx}2$ (step S34: Yes), the second arithmetic unit 9242C performs a matrix operation of multiplying the input image signals, which are RGB signals, by a matrix coefficient (step S35).

Thereafter, the control unit 9245C outputs the operation result of the second arithmetic unit 9242C to the gamma correction unit 927 (step S36).

When the determination unit 9244C has determined in step S34 that the input image signals ($R_{img}$, $G_{img}$, $B_{img}$) do not satisfy $R_{img} \approx R_{mtx}2$, $G_{img} \approx G_{mtx}2$, and $B_{img} \approx B_{mtx}2$ (step S34: No), the third arithmetic unit 9243C performs a matrix operation of multiplying the input image signals, which are RGB signals, by a matrix coefficient (step S37).

Thereafter, the control unit 9245C outputs the operation result of the third arithmetic unit 9243C to the gamma correction unit 927 (step S38).

According to the third embodiment described above, since the linear matrix operation may be performed using the optimum matrix coefficient in accordance with the input color, it is possible to further improve the color reproducibility. Although the third embodiment is an example of having three arithmetic units, the number of arithmetic units may be four or more.

Figure 12:
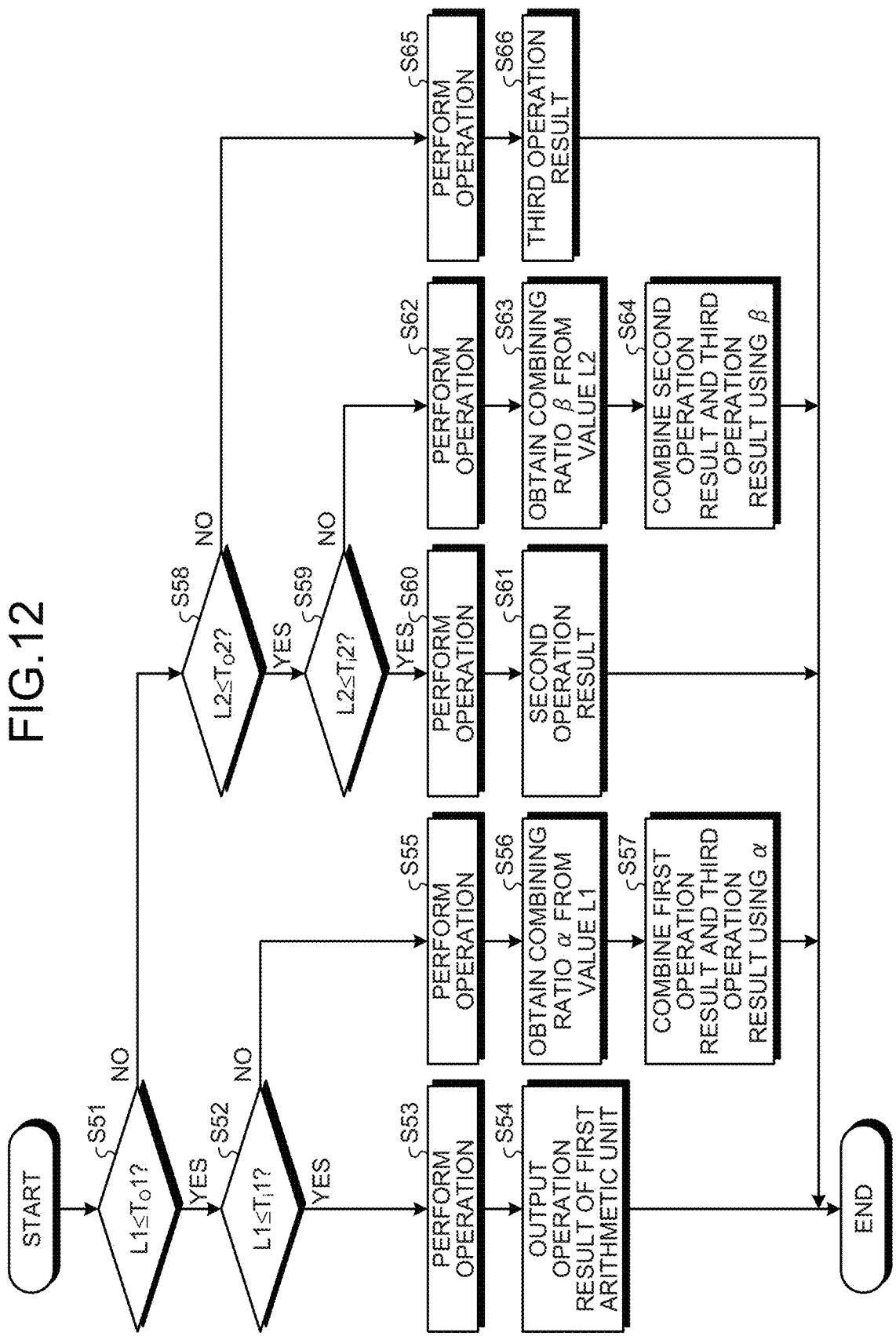
FIG. 12 is a flowchart illustrating an outline of processing executed by the linear matrix operation unit.

Furthermore, when combining the operation results of the arithmetic unit as in the second embodiment, the operation results of a plurality of arithmetic units may be combined. FIG. 12 is a flowchart illustrating an outline of the processing executed by the linear matrix operation unit 924C in this case. Since the configuration of the linear matrix operation unit is substantially the same, the description thereof will be omitted.

As illustrated in FIG. 12, the determination unit 9244C first determines whether the distance L1 is within the first threshold $T_o1$ (step S51).

When the determination unit 9244C determines that the distance L1 is within the first threshold $T_o1$ (step S51: Yes), the determination unit 9244C determines whether the distance L1 is within a third threshold $T_i1$ ($T_i1<T_o1$) (step S52).

When the determination unit 9244C has determined that the distance L1 is within the third threshold $T_i1$ (step S52: Yes), the first arithmetic unit 9241C performs a matrix operation of multiplying the input image signals, which are RGB signals, by a matrix coefficient (step S53).

Thereafter, the control unit 9245C outputs the operation result of the first arithmetic unit 9241C to the gamma correction unit 927 (step S54).

When the determination unit 9244C has determined that the distance L1 is greater than the third threshold $T_i1$ (step S52: No), the first arithmetic unit 9241C and the third arithmetic unit 9243C perform matrix operations of multiplying the input image signals which are RGB signals by the matrix coefficient (step S55).

Thereafter, the control unit 9245C calculates a combining ratio $\alpha$ ($0 \leq \alpha \leq 1$) for combining the operation results of the first arithmetic unit 9241C and the third arithmetic unit 9243C based on the distance L1 (step S56). For example, the combining ratio $\alpha$ is set such that the greater the distance L1, the smaller the value of the ratio $\alpha$.

Based on the combining ratio $\alpha$, the control unit 9245C combines the operation result ($R_{lmtout}1$, $G_{lmtout}1$, $B_{lmtout}1$) of the first arithmetic unit 9241C and the operation result ($R_{lmtout}3$, $G_{lmtout}3$, $B_{lmtout}3$) of the third arithmetic unit 9243C, and then outputs the combining result {$R_{lmtout}1 \times \alpha + R_{lmtout}3 \times (1-\alpha)$, $G_{lmtout}1 \times \alpha + G_{lmtout}3 \times (1-\alpha)$, $B_{lmtout}1 \times \alpha + B_{lmtout}3 \times (1-\alpha)$} to the gamma correction unit 927 (step S57).

When having determined that the distance L1 is greater than the first threshold $T_o1$ (step S51: No), the determination unit 9244C determines whether the distance L2 is within the second threshold $T_o2$ (step S58).

When the determination unit 9244C has determined that the distance L2 is within the second threshold S58: Yes), the determination unit 9244C determines whether the distance L2 is within a fourth threshold $T_i2$ ($T_i2<T_o2$) (step S59).

When the determination unit 9244C determines that the distance L2 is within the fourth threshold $T_i2$ (step S59: Yes), the second arithmetic unit 9242C performs matrix operation of multiplying the input image signals, which are RGB signals, by the matrix coefficient (step S60).

Thereafter, the control unit 9245C outputs the operation result of the second arithmetic unit 9242C to the gamma correction unit 927 (step S61).

When the determination unit 9244C has determined that the distance L2 is greater than the fourth threshold $T_i2$ (step S59: No), the second arithmetic unit 9242C and the third arithmetic unit 9243C perform matrix operations of multiplying the input image signals, which are RGB signals, by matrix coefficients (step S62).

Thereafter, the control unit 9245C calculates a combining ratio $\beta$ ($0 \leq \beta \leq 1$) for combining the operation results of the second arithmetic unit 9242C and the third arithmetic unit 9243C based on the distance L2 (step S63). For example, the combining ratio $\beta$ is set such that the greater the distance L2, the smaller the value of the ratio $\beta$.

Based on the combining ratio $\beta$, the control unit 9245C combines the operation result ($R_{lmtout}2$, $G_{lmtout}2$, $B_{lmtout}2$) of the second arithmetic unit 9242C and the operation result ($R_{lmtout}3$, $G_{lmtout}3$, $B_{lmtout}3$) of the third arithmetic unit 9243C, and then outputs the combining result {$R_{lmtout}2 \times \beta + R_{lmtout}3 \times (1-\beta)$, $G_{lmtout}2 \times N + G_{lmtout}3 \times (1-\beta)$, $B_{lmtout}2 \times \beta + B_{lmtout}3 \times (1-\beta)$} to the gamma correction unit 927 (step S64).

When the determination unit 9244C has determined that the distance L2 is greater than the second threshold $T_o2$ (step S58: No), the third arithmetic unit 9243C performs a matrix operation of multiplying the input image signals, which are RGB signals, by a matrix coefficient (step S65).

Thereafter, the control unit 9245C outputs the operation result of the third arithmetic unit 9243C to the gamma correction unit 927 (step S66).

In this manner, the combining ratio ($\alpha$, $\beta$) is calculated in accordance with how close the input image signals ($R_{img}$, $G_{img}$, $B_{img}$) are to the first color ($R_{mtx}1$, $G_{mtx}1$, $B_{mtx}1$) or the second color ($R_{mtx}2$, $G_{mtx}2$, $B_{mtx}2$). Furthermore, since the outputs from the arithmetic units (the first arithmetic unit 9241C, the second arithmetic unit 9242C, and the third arithmetic unit 9243C) are combined by the calculated combining ratio, the color reproducibility may be further improved.

Fifth Embodiment

In the image processing apparatus according to a fifth embodiment, the configuration other than the linear matrix operation unit is similar to the configuration of the first embodiment, and thus the description thereof will be omitted.

Configuration of Linear Matrix Operation Unit

FIG. 12 is a diagram illustrating a configuration of a linear matrix operation unit in an image processing apparatus according to the fifth embodiment. As illustrated in FIG. 12, a linear matrix operation unit 924D includes a determination unit 9241D, an arithmetic unit 9242D, and a coefficient modulator 9243D.

The determination unit 9241D determines whether the image signal satisfies a predetermined condition. The determination unit 9241D determines whether the luminance Y calculated by using the operation result in a case where the image signal has been input to the arithmetic unit 9242D, is negative, for example. As a result, the determination unit 9241D detects an image signal having a negative luminance Y in advance. Note that an image signal having a negative luminance Y may be calculated in advance by using a preset matrix coefficient of the arithmetic unit 9242D. With this calculation result stored in the storage unit 97 as a table, the determination unit 9241D may make a determination by referring to this table.

The arithmetic unit 9242D performs a linear matrix operation on the image signal using a predetermined matrix coefficient. Specifically, the arithmetic unit 9242D performs a linear matrix operation on the image signal using a preset matrix coefficient or a matrix coefficient modulated by the coefficient modulator 9243D.

The coefficient modulator 9243D modulates the matrix coefficient of the coefficient modulator 9243D in accordance with the determination result of the determination unit 9241D. Specifically, in a case where the coefficient modulator 9243D has determined that the luminance Y calculated by using the operation result in a case where the determination unit 9241D has input the image signal to the arithmetic unit 9242D, is not negative, the coefficient modulator 9243D would not perform modulation of the matrix coefficient of the arithmetic unit 9242D. In contrast, in a case where the coefficient modulator 9243D has determined that the luminance Y calculated by using the operation result in a case where the determination unit 9241D has input the image signal to the arithmetic unit 9242D, is negative, the coefficient modulator 9243D would perform modulation of the matrix coefficient of the arithmetic unit 9242D. At this time, although the coefficient modulator 9243D modulates the matrix coefficient of the arithmetic unit 9242D into an identity matrix, for example, the mode of modulation is not particularly limited.

Linear Matrix Operation Process

Figure 13:
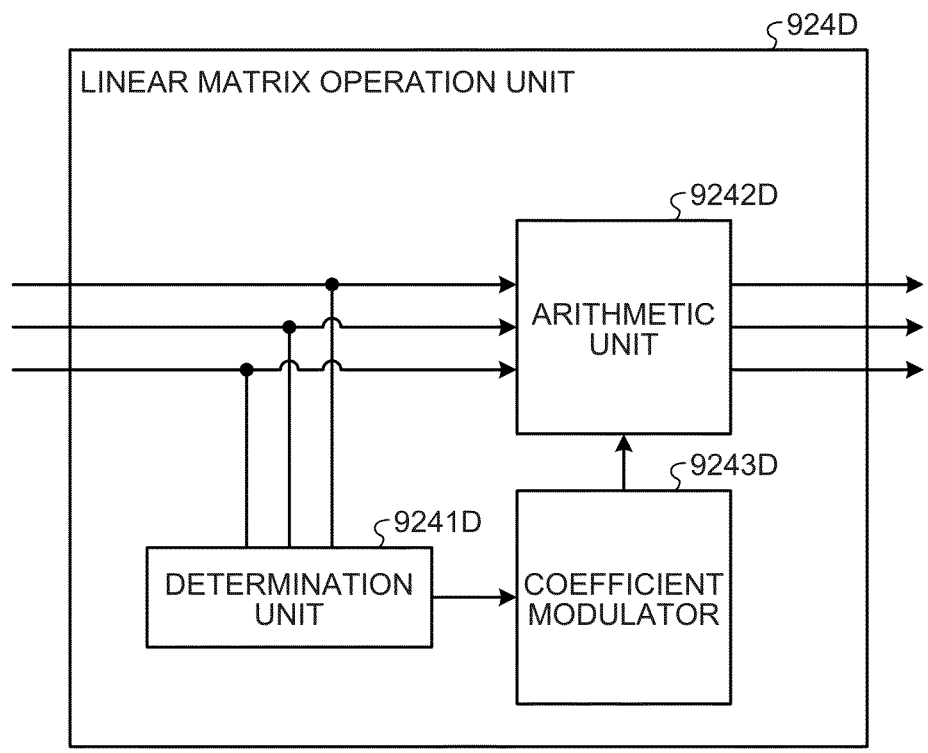
FIG. 13 is a diagram illustrating a configuration of a linear matrix operation unit in an image processing apparatus according to a fifth embodiment.
Figure 14:
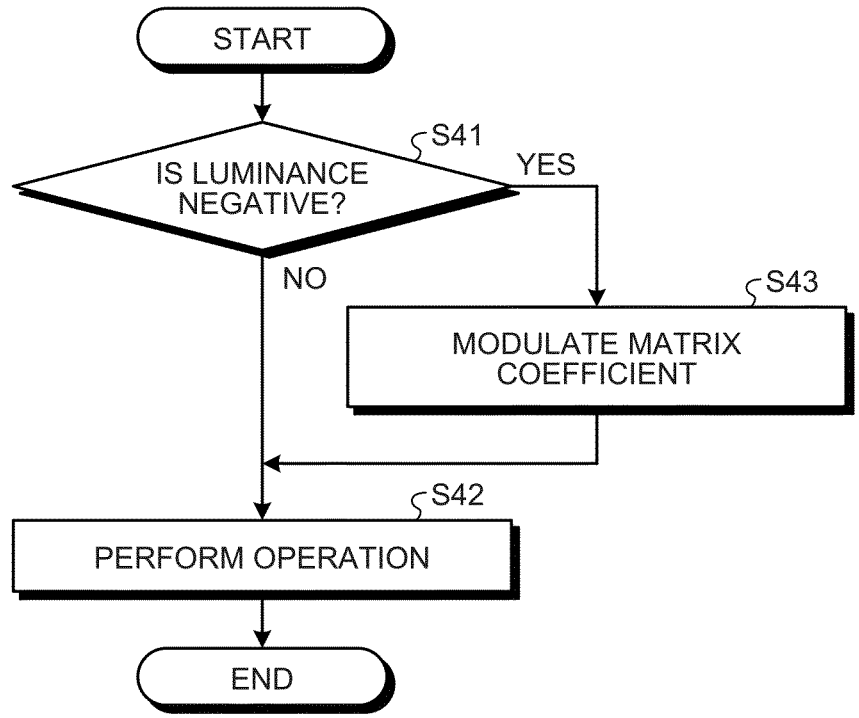
FIG. 14 is a flowchart illustrating an outline of processing executed by the linear matrix operation unit.

FIG. 13 is a flowchart illustrating an outline of processing executed by the linear matrix operation unit. As illustrated in FIG. 13, the determination unit 9241D first determines whether the luminance Y calculated by using the operation result in a case where the image signal has been input to the arithmetic unit 9242D, is negative (step S41).

In a case where the determination unit 9241D has determined that the luminance Y calculated by using the operation result in a case where the image signal has been input to the arithmetic unit 9242D is not negative (step S41: No), the arithmetic unit 9242D performs a matrix operation of multiplying the input image signals, which are RGB signals, by a preset matrix coefficient (step S42).

When the arithmetic unit 9242D has determined that the luminance Y calculated by using the operation result in a case where the image signal has been input to the arithmetic unit 9242D is negative (step S41: Yes), the coefficient modulator 9243D modulates the matrix coefficient of the arithmetic unit 9242D into an identity matrix, for example (step S43).

Thereafter, the arithmetic unit 9242D performs a matrix operation of multiplying the input image signals, which are RGB signals, by the matrix coefficient modulated by the coefficient modulator 9243D (step S42).

According to the fifth embodiment described above, when the luminance Y calculated by using the operation result in the case where the image signal has been input to the arithmetic unit 9242D is not negative, the operation result using the preset matrix coefficient will be output to the gamma correction unit 927, leading to sufficiently good color reproducibility. When the luminance Y calculated by using the operation result in a case where the image signal has been input to the arithmetic unit 9242D is negative, the operation result using matrix coefficient in the form of an identity matrix will be output to the gamma correction unit 927, making it possible to prevent a malfunction of having a negative luminance Y. As illustrated in the fifth embodiment, when the matrix coefficient is modulated, the number of arithmetic units may be one.

In step S41 of FIG. 13, the determination unit 9241D determines whether the luminance Y is negative. Alternatively, however, similarly to the first embodiment, the determination unit 9241D may determine whether the operation result ($R_{lmt}$, $G_{lmt}$, $B_{lmt}$) of the arithmetic unit 9242D satisfies $R_{lmt} > R_{max} \times \delta 1$, $G_{lmt} > G_{max} \times \delta 1$, and $B_{lmt} > B_{max} \times \delta 1$, or satisfies $R_{lmt} < R_{max} \times \delta 2$, $G_{lmt} < G_{max} \times \delta 2$, and $B_{lmt} < B_{max} \times \delta 2$.

Moreover, although the determination unit 9241D determines whether the luminance Y is negative, it may alternatively determine whether $\varepsilon 1 \times Y_{max} < Y < \varepsilon 2 \times Y_{max}$, $Cb > \varepsilon 3 \times Cb_{max}$, and $\varepsilon 4 \times Cr_{max} < Cr < \varepsilon 5 \times Cr_{max}$ are individually satisfied.

Furthermore, the above-described embodiment is an example of application to an image processing apparatus that receives an input of an image signal captured by an endoscope and that performs image processing on the image signal. Alternatively, application is possible to an image processing apparatus that performs image processing on an image signal captured by the imaging devices such as cameras, videos, and microscopes.

Although the preferred embodiments of the present disclosure have been described in detail with reference to the accompanying drawings, the technical scope of the present disclosure is not limited to such examples. It is obvious that a person having ordinary skill in the technical field of the present disclosure may come up with various alterations or modifications within the scope of the technical idea described in the claims, and it is naturally to be understood that these should also belong to the technical scope of the present disclosure.

For example, each of devices described herein may be implemented as a single device, or part or all of the devices may be actualized as a separate device. For example, the control device 9 may be implemented as a single device.

Furthermore, for example, the control device 9 may be implemented as a server device connected to the display device 7 via a network or the like.

Furthermore, the control device 9 described in the present specification may be implemented as a system by having a part or all of individual component actualized as a separate device. For example, the control device 9 may include a light source and an imaging device, and the control unit may be a system implemented by an external device.

In addition, the series of processes by each device described in the present specification may be implemented by using software, hardware, or a combination of software and hardware. The programs constituting the software are stored in advance in, for example, a recording medium or media (non-transitory medium or media) provided inside or outside of the individual devices. In addition, at execution of each of the programs by a computer, for example, the program is loaded to the RAM and executed by a processor such as a CPU.

In addition, the processes described with reference to the flowchart in the present specification do not necessarily have to be executed in the order illustrated. Some processing steps may be performed in parallel. Moreover, additional processing steps may be adopted, and some processing steps may be omitted.

Furthermore, the effects described in the present specification are merely illustrative or exemplary, and are not limiting. That is, the technique according to the present disclosure may have other effects that are apparent to those skilled in the art from the description of the present specification, in addition to or instead of the above effects.

The following configurations also belong to the technical scope of the present disclosure.

(1)

An image processing apparatus including a linear matrix operation unit configured to set a matrix coefficient in accordance with an input image signal, and perform a linear matrix operation on the image signal using the set matrix coefficient.

(2)

The image processing apparatus according to (1), wherein the linear matrix operation unit includes:

a plurality of arithmetic units each of which is configured to perform a linear matrix operation on the image signal using mutually different matrix coefficients;

a determination unit configured to determine whether an operation result of the arithmetic unit satisfies a predetermined condition; and a control unit configured to output the operation result of the arithmetic unit selected in accordance with a result of the determination made by the determination unit.

(3)

The image processing apparatus according to (2), wherein the predetermined condition is whether a luminance calculated by using the operation result of the arithmetic unit is negative.

(4)

The image processing apparatus according to (2), wherein the predetermined condition is whether a luminance calculated by using the operation result of the arithmetic unit and a color difference calculated by using the operation result of the arithmetic unit satisfy predetermined conditions.

(5)

The image processing apparatus according to (1), wherein the linear matrix operation unit includes:

a plurality of arithmetic units each of which is configured to perform a linear matrix operation on the image signal using mutually different matrix coefficients;

a calculation unit configured to calculate a ratio used for combining the operation results of the arithmetic units in accordance with the operation results of the arithmetic units; and a control unit configured to combine the operation results of the arithmetic units based on the ratio calculated by the calculation unit, and output a combined result.

(6)

The image processing apparatus according to (1), wherein the linear matrix operation unit includes:

a determination unit configured to determine whether the image signal satisfies a predetermined condition;

a plurality of arithmetic units each of which is configured to perform a linear matrix operation on the image signal using mutually different matrix coefficients; and a control unit configured to output the operation result of the arithmetic unit selected in accordance with a result of the determination made by the determination unit.

(7)

The image processing apparatus according to (6), wherein the predetermined condition is whether a luminance calculated by using the operation result in a case where the image signal has been input to the arithmetic unit, is negative.

(8)

The image processing apparatus according to (6), wherein the predetermined condition is whether a luminance calculated by using the operation result in a case where the image signal has been input to the arithmetic unit and a color difference calculated by using the operation result in a case where the image signal has been input to the arithmetic unit satisfy predetermined conditions.

(9)

The image processing apparatus according to (1), wherein the linear matrix operation unit includes:

a plurality of arithmetic units each of which is configured to perform a linear matrix operation on the image signal using mutually different matrix coefficients; and a control unit configured to calculate a ratio used for combining the operation results of the arithmetic units in accordance with the image signal, combine the operation results of the arithmetic units based on the ratio, and output a combined result.

(10)

The image processing apparatus according to (1), wherein the linear matrix operation unit includes:

a determination unit configured to determine whether the image signal satisfies a predetermined condition;

an arithmetic unit configured to perform a linear matrix operation on the image signal; and a coefficient modulator configured to modulate a matrix coefficient of the arithmetic unit in accordance with a result of the determination made by the determination unit.

(11)

The image processing apparatus according to any one of (1) to (10), wherein the linear matrix operation unit is configured to output the image signal in a case where the image signal satisfies a predetermined condition.

(12)

An image processing method including: setting a matrix coefficient in accordance with an input image signal; and performing a linear matrix operation on the image signal using the set matrix coefficient.

According to the present disclosure, it is possible to provide an image processing apparatus and an image processing method capable of preventing malfunction while ensuring color reproducibility in the linear matrix operation.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An image processing apparatus comprising:
   a processor configured to
      set a matrix coefficient in accordance with an input image signal, and
      perform a linear matrix operation on the image signal using the set matrix coefficient, wherein
   the processor including a plurality of arithmetic units each of which is configured to perform a linear matrix operation on the image signal using mutually different matrix coefficients, and
   the processor further configured to
      determine whether an operation result of an arithmetic unit of the plurality of arithmetic units satisfies a predetermined condition, the predetermined condition being whether a luminance calculated by using the operation result of the arithmetic unit is negative,
      output the operation result of the arithmetic unit selected in accordance with a result of the determination made by the processor, and
      output the image signal in a case where the image signal satisfies another predetermined condition.

2. The image processing apparatus according to claim 1, wherein the predetermined condition is whether a luminance calculated by using the operation result of the arithmetic unit and a color difference calculated by using the operation result of the arithmetic unit satisfy predetermined conditions.

3. The image processing apparatus according to claim 1, wherein
   the processor is configured to calculate a ratio used for combining the operation results of the arithmetic units in accordance with the operation results of the arithmetic units,
   combine the operation results of the arithmetic units based on the ratio calculated by the processor, and
   output a combined result.

4. The image processing apparatus according to claim 1, wherein the predetermined condition is whether the luminance calculated by using the operation result in a case where the image signal has been input to the arithmetic unit and a color difference calculated by using the operation result in a case where the image signal has been input to the arithmetic unit satisfy predetermined conditions.

5. The image processing apparatus according to claim 1, wherein
   the processor is further configured to
      calculate a ratio used for combining the operation results of the arithmetic units in accordance with the image signal,
      combine the operation results of the arithmetic units based on the ratio, and
      output a combined result.

6. The image processing apparatus according to claim 1, wherein the
   processor is further configured to modulate a matrix coefficient of the arithmetic unit in accordance with a result of the determination made by the processor.

7. An image processing method comprising:
   setting a matrix coefficient in accordance with an input image signal;
   performing, with a processor, a linear matrix operation on the image signal using the set matrix coefficient, the processor including a plurality of arithmetic units each of which is configured to perform a linear matrix operation on the image signal using mutually different matrix coefficients;
   determining with the processor whether an operation result of an arithmetic unit of the plurality of arithmetic units satisfies a predetermined condition, the predetermined condition being whether a luminance calculated by using the operation result of the arithmetic unit is negative;
   outputting the operation result of the arithmetic unit selected in accordance with a result of the determination made by the processor; and
   outputting the image signal in a case where the image signal satisfies another predetermined condition.

* * * * *